(12) United States Patent
Tsuzuki et al.

(10) Patent No.: US 7,022,523 B2
(45) Date of Patent: Apr. 4, 2006

(54) CARRIER FOR CELL CULTURE

(75) Inventors: Hirohiko Tsuzuki, Minami-ashigara (JP); Satoru Toda, Minami-ashigara (JP); Makoto Kato, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 33 days.

(21) Appl. No.: 10/691,506

(22) Filed: Oct. 24, 2003

(65) Prior Publication Data

US 2004/0157328 A1 Aug. 12, 2004

(30) Foreign Application Priority Data

Oct. 24, 2002 (JP) ............................. 2002-309124
Feb. 26, 2003 (JP) ............................. 2003-049251

(51) Int. Cl.
*C12N 5/00* (2006.01)
(52) U.S. Cl. ...................................... 435/401; 435/397
(58) Field of Classification Search ............... 424/93.7; 435/401, 397, 178, 198, 402
See application file for complete search history.

(56) References Cited

U.S. PATENT DOCUMENTS 5,116,824 A * 5/1992 Miyata et al. ................. 514/55

FOREIGN PATENT DOCUMENTS

WO   WO 9109119 A1 * 6/1991

OTHER PUBLICATIONS

Huguet ML and Dellacherie E, "Calcium alginate beads coated with chitosan: effect of the structure of encapsulated materials on their release" Process Biochemistry, 1996 31(8): 745-751, entire document.*

* cited by examiner

*Primary Examiner*—Jean Witz
*Assistant Examiner*—Satyendra K. Singh
(74) *Attorney, Agent, or Firm*—Sughrue Mion, PLLC

(57) ABSTRACT

A carrier for cell culture comprising a water-containing polymer gel containing chitosan, wherein the water-containing polymer gel is coated with collagen and/or alginic acid, and a carrier for cell culture, which comprises a gel layer containing chitosan and an inorganic layer adjacently provided to the gel layer.

6 Claims, 1 Drawing Sheet

CARRIER FOR CELL CULTURE

TECHNICAL FIELD

The present invention relates to a technique for cell culture. More specifically, the present invention relates to a carrier for cell culture and a method for culturing cells utilizing the carrier for cell culture, and also to a cell culture that can be obtained by the method for cell culture.

BACKGROUND ART

A water-containing polymer gel has a structure similar to that of a living body, and has a property of expanding or shrinking depending on external conditions such as temperature, acidity, and alkalinity. Accordingly, applications in the medical field, including a use as an artificial organ or tissue such as an artificial muscle or encapsulation of a drug therein to control an amount to be released, have been attempted, as well as applications as an anchorage of cell growth in a cell culture as a gel containing various kinds of cytokines and the like.

It is known that cells are arrayed with polarity when they form a tissue in a living body. For example, hepatocytes absorb blood components from the vascular endothelial cell side, and excrete metabolites such as bile acid from the opposite side. Since this bile acid has potent cytotoxicity, cell culture by adhering the cells on an ordinary petri dish for cell culture suffers from a problem that stable long-term culture is difficult. Although it is also known that the polarity of cells is expressed by stimulation given from one way to the cells, cell culture by adhering the cells on an ordinary petri dish for cell culture causes a problem that stimulation cannot be given from the adhesion side.

To solve these problems, a permeable collagen membrane for cell culture, MEN-01, is sold by KOKEN CO., LTD. as a cell culture material for culturing cells with different media for the both sides of the cells. However, in this product, the collagen membrane is much swelled with a medium, and thus the product is significantly distorted during the culture. Therefore, it is difficult to observe a culture state of cells. Further, a carrier for cell culture is proposed which comprises a porous membrane together with an alginic acid gel layer and an extracellular matrix component gel layer or an extracellular matrix component sponge layer, which are laminated on the porous membrane (Japanese Patent Unexamined Publication (KOKAI) No. 2001-120267). However, this carrier for cell culture has a microfilter layer, and therefore, growth state of cells cannot be observed under an optical microscope. Furthermore, a polymer complex of chitosan and an anionic cellulose derivative is proposed as a carrier for cell culture (Japanese Patent Unexamined Publication (KOKAI) No. 6-277038). However, chitosan and the anionic cellulose derivative will form a gel immediately after mixing, and therefore it is difficult to obtain a carrier for cell culture having a flat and smooth surface.

As further problems, since such a gel swells after immersion in a medium to lose strength, it is difficult to take out a cell culture out of the medium. In addition, since the gel cannot be attached only to a minute space, the gel was also unsuitable for construction of cell chips in which cells are divided into minute spaces and cultured.

DISCLOSURE OF THE INVENTION

An object of the present invention is to provide a carrier for cell culture that can solve the aforementioned problems. More specifically, the object of the present invention is to provide a carrier for cell culture which enables culture of cells with a different medium for each face of the cells and convenient observation of growth state of the cells under an optical microscope. Another object of the present invention is to provide a carrier for cell culture having the aforementioned characteristics, which further has superior strength after culture. The inventors of the present invention conducted various studies to achieve the foregoing objects. As a result, they found that the aforementioned objects were successfully achieved by the means described below, and thus accomplished the present invention.

The present invention thus provides a carrier for cell culture comprising a water-containing polymer gel containing chitosan, wherein the water-containing polymer gel is coated with collagen and/or alginic acid. According to preferred embodiments of this invention, there are provided the aforementioned carrier for cell culture, which comprises two or more coated layers; the aforementioned carrier for cell culture, wherein an outermost layer is a collagen-coating layer or an alginic acid-coating layer; the aforementioned carrier for cell culture, wherein an outermost layer is an alginic acid-coating layer; and the aforementioned carrier for cell culture, which comprises a chitosan-coating layer as an outermost layer formed on an alginic acid-coating layer.

From another aspect, the present invention provides a carrier for cell culture, which comprises a gel layer containing chitosan and an inorganic layer adjacently provided to the gel layer. According to preferred embodiments of the invention, the inorganic layer comprises a metal and/or a metal oxide, and said layer may be formed as a layer containing inorganic microparticles. Preferred examples of the inorganic layer include a stainless steel layer, aluminum layer and the like. According to a further preferred embodiment of the invention, there is provided the aforementioned carrier for cell culture, wherein the inorganic layer has at least one, preferably two or more, of hole or holes having a diameter of 10 μm or more.

According to still further preferred embodiments of the invention, there are provided the aforementioned carrier for cell culture, wherein at least one gel layer containing a cell adhesion component is laminated; the aforementioned carrier for cell culture, wherein the cell adhesion component is selected from the group consisting of collagen and alginic acid; the aforementioned carrier for cell culture, wherein at least one gel layer selected from the group consisting of a collagen layer and an alginic acid layer is laminated; the aforementioned carrier for cell culture, wherein a collagen layer and an alginic acid layer are alternately laminated; and the aforementioned carrier for cell culture, which contains one or more laminated chitosan layers.

From further aspects, the present invention provides a method for cell culture, which comprises the step of culturing cells by using the aforementioned carrier for cell culture, and a cell culture obtained by the aforementioned method.

BEST MODE FOR CARRYING OUT THE INVENTION

Figure 1:
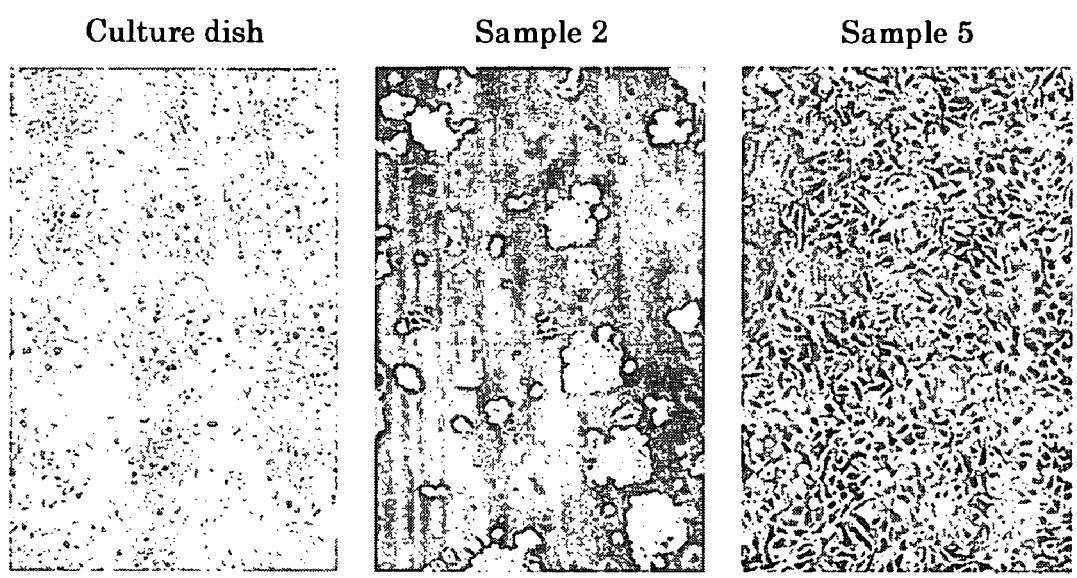
FIG. 1 depicts optical microphotographs showing results of cell culture performed by using a dish for cell culture and the carriers for cell culture of the present invention (Samples 2 and 5).

The carrier for cell culture of the present invention is characterized to comprise a water-containing polymer gel containing chitosan, and the surface of the water-containing gel is coated with collagen and/or alginic acid. Further, the carrier for cell culture of the present invention according to another aspect is characterized to comprise a gel layer containing chitosan and an inorganic layer adjacently provided to the gel layer.

The term "carrier for cell culture" used in the specification means an element that can serve as a carrier or support during cell culture, and this term should not be construed any limitative way. For example, a carrier for cell culture is described in Japanese Patent Unexamined Publication (KO-KAI) No. 2001-120267, in which an alginic acid gel layer and an extracellular matrix component gel layer as a cell adhesion component gel layer are laminated on a porous membrane, and the carrier for cell culture of the present invention can be used for culture in the same technical field similar as that of the carrier for cell culture described in the above patent document.

The gel containing chitosan means a gel that contains chitosan gel as a main component. The water-containing polymer gel containing chitosan means a water-containing polymer gel containing "chitosan gel" as a main component (in the specification, a water-containing polymer gel containing chitosan may also be henceforth referred to as a "chitosan gel"). As the chitosan gel, a gel can be used which does not dissolve in a neutral region in which cell culture is performed. For example, a chitosan gel formed as a gel, which does not dissolve in a neutral region in which cell culture is performed, by neutralizing the amino groups in the molecules of chitosan, a chitosan gel formed as a gel by salt formation of chitosan and an organic polymer compound having an anionic residue, a chitosan gel formed as a gel by crosslinking with a crosslinking agent and the like can be utilized. As the organic polymer compound having an anionic residue, for example, natural or synthetic polymer compounds such as polyaspartic acid, alginic acid, dextran sulfate, chondroitin sulfate, and polystyrenesulfonic acid can be used. Examples of the crosslinking agent include compounds having two or more groups that react with amino group or hydroxyl group such as glutaraldehyde, divinyl sulfone, and halogenated triazine, compounds having two or more carboxylic acid groups which are made into active esters beforehand and the like.

Chitosan (β-poly D-glucosamine) can be obtained by heating chitin (β-poly-N-acetyl-D-glucosamine) with a concentrated alkali solution or subjecting chitin to potassium fusion, and then deacetylating the resultant. Any chitosan can be used for manufacture of the carrier for cell culture of the present invention. For example, from a viewpoint of formation of a membrane having a high membrane strength, preferred is chitosan having a deacetylation degree of from 60 to 100%, and providing a solution viscosity of from 10 to 10000 cP when dissolved at 0.5 mass % in 1 mass % aqueous acetic acid solution. More preferred is chitosan having a deacetylation degree of from 70 to 100%, and providing the solution viscosity of from 40 to 5000 cP.

The gelation of chitosan can be performed in a conventional manner. For example, an acidic solution of chitosan can be applied to a substrate, dried, and then subjected to a neutralization treatment to attain the gelation. More specifically, an application solution prepared by dissolving chitosan in an aqueous acetic acid can be applied to a substrate surface with a desired thickness, and dried, and the obtained membrane can be immersed into aqueous sodium hydroxide, or a buffer having an approximately neutral pH. Chitosan is thereby neutralized, and thus a chitosan gel is obtained. A dry membrane thickness of the gel layer containing chitosan is not particularly limited. The thickness is, for example, preferably from 1 to 20,000 μm, more preferably from 5 to 500 μm. In the specification, the dry membrane thickness of a gel layer is usually a thickness of the gel measured for the gel in a sufficiently dried state, for example, a state that moisture contained in the gel is 100 mass % or less of the total weight of the gel.

The gel containing chitosan may be crosslinked by chemical bonds or ionic bonds. For the crosslinking by chemical bonds, compounds having two or more reactive groups, for example, dialdehydes (glutaraldehyde and the like), divinyl sulfones (divinylsulfonylmethane, N,N'-di(1-vinylsulfonylacetyl)ethylenediamine and the like), triazines (cyanuric chloride, 2,4-dichloro-1-hydroxy-1,3,5-triazine and the like) may preferably be used. For the crosslinking by ionic bonds, polybasic acids (phthalic acid, maleic acid, adipic acid and the like), synthetic anionic polymer compounds (polymer of acid radical-containing monomers such as acrylic acid, methacrylic acid, and styrenesulfonic acid, and copolymers thereof with other monomers), natural anionic polymer compounds or anionic polymer compounds derived form natural substances (alginic acid, hyaluronic acid, chondroitin sulfate, dextran sulfate, agaropectin, carragheenan, carboxymethylcellulose and the like), and amphoteric polymers (gelatin and the like) may preferably be used.

The concentration of the chitosan aqueous solution for preparing the chitosan gel is preferably from 0.01 to 10 mass %, most preferably from 0.1 mass % to 5 mass %. When the solubility of chitosan is insufficient, an acid may be added to dissolve chitosan. As the acid, for example, acetic acid, hydrochloric acid, phosphoric acid and the like can be used. The acidic solution of chitosan for preparing chitosan gel may contain a surface active agent or an organic solvent for adjusting surface tension and viscosity, as well as one or more kinds of additives among various additives usually used for manufacture of gels. Further, in the preparation of the chitosan gel, a degassing step for eliminating air bubbles contained in the acidic solution of chitosan before the application thereof may be employed. The degassing method is not particularly limited, and for example, liquid membrane degassing, vacuum degassing, centrifugal degassing, ultrasonic degassing, or a combination thereof is preferably used. In the manufacture of the chitosan gel, one or more kinds of suitable additives may be added as required. Examples of such additives include, besides the aforementioned surface active agent and organic solvent, antiseptic, pH modifier, dye and the like However, the additives are not limited to these examples.

A method for coating the chitosan gel with collagen is not particularly limited. The coating is preferably attained by, for example, the application method or the immersion method. The application method generally includes the step of applying a collagen aqueous solution to a surface of a gel to be coated, and the steps of washing with water and drying may be optionally employed after the application. The immersion method generally includes the step of adhering a collagen layer to the gel surface by immersing the gel to be coated in an aqueous solution of collagen, and the steps of washing with water and drying may be optionally employed after the immersion. A concentration of the collagen aqueous solution used for these methods is not particularly limited. The concentration is, for example, preferably from 1 ng/L to 50 mg/L, more preferably from 1 μg/L to 10 mg/mL. The type of collagen is not particularly limited. The collagen may be, for example, any of type I, type II, type III, type IV, type V collagens and the like. Further, collagen made into lower molecules with an enzyme, collagen of which telopeptides are digested, collagen prepared by a genetic engineering technique and the like can also be used. Collagen solubilized in an acidic solution can be preferably used.

A method for coating chitosan gel with alginic acid is not particularly limited. The coating is preferably attained by, for example, the application method or the immersion method. The application method generally includes the step of applying an alginic acid aqueous solution to a surface of gel to be coated, and the steps of washing with water and drying may be optionally employed after the application. The immersion method generally includes the step of adhering an alginic acid layer to the gel surface by immersing the gel to be coated in an aqueous solution of alginic acid, and the steps of washing with water and drying may be optionally employed after the immersion.

The alginic acid gel means alginic acid gelled by a chelate structure formed with a carboxylic acid group in the molecule of alginic acid and a polyvalent metal ion, and "alginic acid gel layer" means alginic acid gel in the form of a layer. Alginic acid is a block copolymer consisting of glucuronic acid (G) and mannuronic acid (M), and it is considered that the polyvalent metal cation enters into a pocket structure of the M block to form an egg box and thereby cause the gelation. Specific examples of the polyvalent metal cation that can cause the gelation of alginic acid include, for example, metal ions such as barium, lead, copper, strontium, cadmium, calcium, zinc, nickel, cobalt, manganese, iron and magnesium ions. Among them, divalent metal ions are preferred, and examples include calcium ion, magnesium ion, barium ion and strontium ion. Particularly preferred is calcium ion. The "alginic acid gel" may be a polyion complex gel of alginic acid and an organic polymer compound having a cationic residue. Examples of the organic polymer compound having a cationic residue include compounds having two or more amino groups such as polylysine, chitosan, gelatin, and collagen. The method for gelation of alginic acid is not particularly limited, and it may be performed in a conventional manner. For example, the gelation of alginic acid can be performed by utilizing ion exchange. For example, when calcium ions are added to an aqueous solution of sodium alginate, ion exchange quickly occurs to give calcium alginate gel.

Alginic acid exists in nature as a cell wall-constituting polysaccharide or intercellular filling substance of brown algae, and can be obtained from the algae as raw materials. Examples of the brown algae as a raw material include brown algae belonging to Order Fucales, Family Durvilleaceae, Genus *Durvillea* (e.g., *D. potatorum*), Order Fucales, Family Fucaceae, Genus *Ascophyllum* (e.g., *A. nodosum*), Order Laminariales, Family Laminariaceae, Genus *Laminaria* (e.g., *Laminaria japonica, Laminaria longissima*), Order Laminariales, Family Laminariaceae, Genus *Eisenia* (e.g., *Eisenia bicyclis*), Order Laminariales, Family Laminariaceae, Genus *Ecklonia* (e.g., *Ecklonia cava, Ecklonia kurome*), and Order Laminariales, Family Lessoniaceae, Genus *Lessonia* (e.g., *L. flavikans*). Commercially available alginic acid can also be used. A G/M ratio of alginic acid is not particularly limited. A larger G/M ratio provides a higher gel formation ability, and accordingly, a larger G/M ratio is more preferred. Specifically, the ratio may preferably be from 0.1 to 1, more preferably from 0.2 to 0.5. The concentration of the aqueous solution of sodium alginate for the preparation of alginic acid gel is preferably from 1 mg/L to 10 g/L, particularly preferably from 10 mg/L to 5 g/mL.

For producing the carrier for cell culture of the present invention, the chitosan gel may be coated with a mixture of collagen and alginic acid. It is also possible to blend chitosan in such a mixture. Further, after the surface of the chitosan gel is coated with alginic acid, and then the surface may be further coated with collagen, or after the surface of the chitosan gel is coated with collagen, the surface may be further coated with alginic acid. Coating with collagen and coating with alginic acid may be repeated to form a coating of multilayer structure. In such an embodiment, coating of chitosan or other polymers may be used as one or more of the layers of the multilayer structure. A structure of such multilayer is not particularly limited. The structure may generally be formed so that the outermost layer is a collagen coating or alginic acid coating, or a coating of a mixture thereof. Alternatively, a coating of chitosan can be formed on a coating of alginic acid so that the coating of chitosan is the outermost layer. Such a chitosan coating as the outermost layer may be blended with alginic acid and/or collagen.

A method for forming a coating of chitosan is not particularly limited. The coating is preferably attained by, for example, the application method or the immersion method. The application method generally includes the step of applying a chitosan aqueous solution to a surface of gel to be coated, and the steps of washing with water and drying may be optionally employed after the application. The immersion method generally includes the step of adhering a chitosan layer to the gel surface by immersing the gel to be coated in an aqueous solution of chitosan, and the steps of washing with water and drying may be optionally employed after the immersion. A concentration of the chitosan aqueous solution used for the application method and the immersion method is not particularly limited. The concentration may be, for example, preferably from 1 mg/L to 10 g/L, more preferably from 10 mg/L to 5 g/mL.

A method of successively coating various polymer compounds including collagen, alginic acid, and chitosan on the gel surface is not particularly limited. The layer-by-layer method (Gero Decher, Science, No. 277, pp.1232–1237, Aug. 29, 1997,) is preferably used, for example. The layer-by-layer method comprises repeating immersion of a membrane in an aqueous solution of any one of various polymer compounds, subsequent washing with water and immersion in another polymer compound. For producing the carrier for cell culture of the present invention, surface modification for the surface of the water-containing polymer gel containing chitosan can be performed for both sides or one side of the water-containing polymer gel. For performing the modification for one side, a method of attaching a cover on one side, during the aforementioned modification method based on application or the aforementioned modification method based on immersion, is preferably used so that said side is not brought into contact with an immersion solution. For the gelation, a gelling agent may be used, if needed.

In the carrier for cell culture according to the second aspect of the present invention, the inorganic layer is provided adjacently to the gel layer containing chitosan. The term "adjacent" used in the specification means a state that one side of the gel layer containing chitosan and one side of the inorganic layer, each of which layers is generally formed as a plane, are in contact with each other in most of the surface areas of the both. Preferably, any other layer does not exist between the gel layer containing chitosan and the inorganic layer, and they maintain a close contact state.

The inorganic layer may be a layer of a substance selected from the group consisting of a metal and a metal oxide. The type of the metal is not particularly limited so long as the metal is not corrosive. For example, aluminum, silicon, gold, platinum, iron, titanium, tin plate and the like, as well as stainless steel, can be used. As for the metal oxide, any metal oxides almost insoluble in water may be used without particular limitation. Examples include, for example,. titanium oxide, aluminum oxide, zirconium oxide, silicon oxide, iron oxide and the like The inorganic layer may be that contains an inorganic salt hardly soluble in water.

Further, the inorganic layer may be that contains inorganic particles. As the inorganic particles, for example, particles having a particle size of from 1 nm to 1 mm can be used. More specifically, the inorganic particles are those selected from the group consisting of particles of metals, metal oxides hardly soluble in water, inorganic salts hardly soluble in water and the like, and preferably, the particles have a particle size of from 10 nm to 100 µm. In order to form the inorganic layer containing inorganic particles, a binder can usually be used. The type of the binder is not particularly limited, and the layer can be formed so as to contain one or more kinds of organic or inorganic binders.

For example, when a stainless steel layer is used as the inorganic layer, a stainless steel thin plate may be used as the inorganic layer without any treatment. Thin plates of other metals can be used in the same manner. Alternatively, the inorganic layer may be formed on another substrate such as a polymer substrate and a substrate made of paper. For example, an aluminum thin membrane formed by vapor deposition on a surface of a polymer substrate can also be used as an aluminum layer. A thickness of the inorganic layer is not particularly limited. For example, the thickness may preferably be from 1 nm to 10 mm, more preferably from 10 nm to 2 mm.

The inorganic layer preferably has one or more holes having a diameter of 10 µm or more. The diameter of the holes is not particularly limited. For example, the diameter may preferably be from 10 µm to 1 m, more preferably from 20 µm to 30 cm, and most preferably from 50 µm to 10 cm. The holes enable supply and discharge of substances also from the culture carrier side, as well as from the medium side, and also enable observation of a cell layer or morphology of cells formed on the carrier for cell culture by using a transmission inverted microscope. The number of the holes is not particularly limited, and the number may preferably be from 12 to 100,000. The size and number of the holes are preferably adjusted so that the total area of the holes per square meter can be in the range of from 0.01 to 0.99 square meters, preferably from 0.1 to 0.9 square meters.

In the carrier for cell culture of the present invention, it is desirable to provide a gel layer containing chitosan on one side or both sides of the inorganic layer. Among the surfaces of the gel containing chitosan, the surface not adjacent to the inorganic layer can be used for cell culture as the outermost surface. On the chitosan surface, at least one gel layer containing a cell adhesion component may be laminated. In the specification, "laminated" means a state that two or more layers were piled. As the cell adhesion component, collagen, alginic acid, chitosan and the like can be used, for example. It is also preferred that such a gel layer consists of two or more of layers. For example, it is preferred that a gel layer containing alginic acid and a gel layer containing chitosan are laminated, and it is preferred that at least two, preferably three or more, of the gel layers containing alginic acid and the gel layers containing chitosan are alternately laminated. Two or more layers containing the same component may be laminated. The outermost layer may be either the gel layer containing alginic acid, or the gel layer containing chitosan. Further, a gel layer containing collagen may be provided as an intermediate layer or the outermost layer.

When the gel layer containing chitosan is formed, the layer formation can be performed by any method. The methods explained above are preferably employed. For example, the surface modification is preferably performed by the application method or the immersion method. In the application method, a chitosan aqueous solution is applied to a gel surface, and the steps of washing with water and drying may be optionally added after the application. The immersion method is to adhere a gel layer containing chitosan to the gel surface by immersing the gel membrane in a chitosan aqueous solution, and the steps of washing with water and drying may be optionally added after the immersion. The concentration of the chitosan aqueous solution used for the surface modification is preferably from 1 mg/L to 10 g/L, more preferably from 10 mg/L to 5 g/mL.

A method of use of the carrier for cell culture of the present invention is not particularly limited. For example, the carrier for cell culture can be attached to a bottom surface of a cylinder, and culture can be performed by using a different medium each for inside and outside of the carrier. Further, the carrier for cell culture of the present invention can be used as a carrier for cell culture for the so-called circumfusion culture by providing the same at an interface of flows of two kinds of media. In the carrier for cell culture according to the first aspect of the present invention, the inside or back surface of the chitosan gel may be reinforced with fibers, net and the like to meet such various purposes of use. Such means can be suitably chosen by those skilled in the art depending on a purpose.

By using the carrier for cell culture of the present invention, cells can be cultured on the surface of the outermost layer. Types of cells that can be cultured are not particularly limited. Specific examples thereof include, for example, fibroblasts, vascular endothelial cells, chondrocytes, hepatocytes, small intestine epithelial cells, epidermal keratinocytes, osteoblasts, bone marrow mesenchymal cells, embryonic stem cells, somatic stem cells and the like. For the cell culture, a culture medium (for example, D-MEM medium, MEM medium, HamF12 medium, or HamF10 medium) containing cells at a density of from 10,000 to 15,000 cells/ml is usually added onto the cell adhesion gel layer. The cell culture conditions can be appropriately chosen depending on the type of cells to be cultured. When cells are cultured on the cell adhesion gel layer, in general, the culture can be continued until a confluent cell monolayer is formed on the cell adhesion gel layer.

Culture of cells using the carrier for cell culture of the present invention can be performed specifically as follows. The carrier for cell culture is placed inside a petri dish or the like, then an appropriate culture medium (for example, D-MEM medium, MEM medium, HamF12 medium, HamF10 medium) is added to the petri dish to immerse the carrier for 5 minutes, and then the medium is exchanged. After this procedure is repeated three times, the culture system was left for 12 to 24 hours so that the culture medium can infiltrate into the carrier for cell culture. Then, the culture medium in the petri dish is discarded, and then cells are inoculated onto the outermost layer of the carrier for cell culture, and further an appropriate culture medium (for example, D-MEM medium, MEM medium, HamF12 medium, HamF10 medium) is added to the petri dish. After the system is left at 37° C. for 1 to 2 hours so that the cells can be held by (adhered to) the gel surface of the outermost layer, the culture is continued at 37° C. During the culture, the culture medium may be exchanged, if needed. Usually, the culture medium is exchanged every 0.5 to 2 days of the culture. Cell culture obtained as described above contains the aforementioned carrier for cell culture and a cell layer retained on the carrier for cell culture. The "cell layer retained on the surface of the carrier for cell culture" is a cell layer formed on the surface of outermost layer of the carrier for cell culture.

The carrier for cell culture of the present invention may be sterilized by any method. Sterilization by radiation such as electron beam, γ-ray, X-ray, and ultraviolet ray may preferably be used. An electron beam, γ-ray, and ultraviolet ray are more preferably used, and electron beam sterilization is particularly preferred. An exposure dose for the electron beam sterilization according to the present invention is preferably from 0.1 to 65 kGy, most preferably from 1 to 40 kGy. Chemical sterilization such as ethylene oxide gas sterilization and sterilization using a high temperature such as high pressure steamy gas sterilization may not be preferred, because the cell adhesion layer and the alginic acid gel layer may be decomposed. A carrier for cell culture sterilized as described above can be stored at room temperature for a long period of time, if it is stored under a sterile condition. The aforementioned sterilization methods may be used each alone or in combination. The same sterilization method may be applied repeatedly.

EXAMPLES

The present invention will be more specifically explained by referring to the following examples. However the scope of the present invention is not limited to these examples.

Example 1

Preparation of Carrier for Cell Culture (1) Chitosan Gel Membrane
  (i) Preparation of a Solution for Application of Chitosan
  2.5 g of chitosan (Chirosan 100 produced by Wako Pure Chemical Industries) was dissolved in 98 g of 1 weight % acetic acid aqueous solution.
  (ii) Preparation of Chitosan Gel Membrane
  The solution for chitosan application was applied in a thickness of 1 mm on a polyethylene terephthalate substrate, and the coated layer was dried under the conditions of 35° C. and 30% RH. The dried chitosan membrane was immersed in 0.1 N aqueous sodium hydroxide for 1 hour, and then dried under the conditions of 35° C. and 30% RH to prepare Sample 1. Further, the dried chitosan membrane was immersed in an isotonic sodium phosphate buffer of pH 7.2 instead of the aqueous sodium hydroxide to prepare Sample 2. The both samples had a thickness of 20 μm.

(2) Surface Modification of Gel Membrane
  (i) Preparation of Alginic Acid Aqueous Solution
  Sodium arginate (sodium arginate produced by Wako Pure Chemical Industries, 100 to 150 cP) was dissolved in water at a concentration of 1 weight %.
  (ii) Preparation of Chitosan Aqueous Solution
  1 g of chitosan (Chirosan 100 produced by Wako Pure Chemical Industries) was dissolved in 99 g of 1 weight % acetic acid aqueous solution.
  (iii) Preparation of Collagen Aqueous Solution
  CellmatrixIC (type I collagen aqueous solution produced by Nitta Gelatin) was diluted with water to a concentration of 0.03 mg/ml.
  (iv) Preparation of Alginic Acid-modified Gel Membrane
  Samples 2 obtained in (1), without being dried, was immersed in the alginic acid aqueous solution for 1 hour, and then washed with running water for 1 hour. The sample was further immersed in the chitosan aqueous solution for 1 hour, and then washed with running water for 1 hour. The above operation was repeated three times. Subsequently, the sample was immersed in the alginic acid aqueous solution for 1 hour, washed with running water for 1 hour, and then dried at 35° C., 30% RH to obtain Sample 3.
  (v) Preparation of Chitosan-modified Gel Membrane
  Samples 3, without being dried, was immersed in the chitosan aqueous solution for 1 hour, washed with running water for 1 hour, and then dried at 35° C., 30% RH to obtain Sample 4.
  (vi) Preparation of Collagen-modified Gel Membrane
  Samples 3 and 4, without being dried, were immersed in the collagen aqueous solution for 1 hour, washed with running water for 1 hour, and then dried at 35° C., 30% RH to obtain Samples 5 and 6, respectively. Sample 1 was treated by the same operations as those used for Samples 5 and 6 to prepare Samples 7 and 8, respectively.
  All of Samples 1 to 8 were each dried in a state that the four sides were pinched to prevent deformation of the membrane.

(3) Preparation of Membrane from Chitosan/alginic Acid Mixed Solution
  The alginic acid aqueous solution and chitosan aqueous solution mentioned in the above (2) were mixed in a weight ratio of 1:1, immediately applied, washed with running water, and dried at 35° C., 30% RH to obtain Sample 9. This sample had an extremely wavy surface due to gelation of the solution before the application, and thus a flat and smooth membrane was not obtainable.

The structures and evaluation results for surface condition for Samples 1 to 8 are shown in Table 1. After the obtained membranes were subjected to UV sterilization for 3 hours or electron beam sterilization at 20 kGy, no bacterium was found in each of the membranes. In the samples not subjected to any sterilization treatment, 7,000 cells/m$^2$ of bacteria were observed.

Example 2

Culture of Cells Using Carrier for Cell Culture

Cells were cultured by using the carriers for cell culture as follows.

(1) Used Cell
  CHL (Chinese Hamster Lung Cell)

(2) Used Medium
  Eagle's minimum medium containing 10% fetal bovine serum (3) Carrier for Cell Culture
  Each of the carriers for cell culture of Samples 1 to 9 prepared in Example 1 was adhered to a frame, which was obtained by removing a collagen membrane from a permeable collagen membrane for cell culture, MEN-01, produced by KOKEN CO., LTD., and the permeable collagen membrane for cell culture, MEN-01, produced by KOKEN CO., LTD (comparative example) were put in a polystyrene cell culture dish. The carriers were added with the medium for immersion for 5 minutes, and then the medium was exchanged. This procedure was repeated three times, and then the carriers were left overnight to allow the medium to infiltrate into the carriers for cell culture. Combinations of the used carriers for cell culture and sterilization methods are shown in Table 1.

(4) Inoculation of Cells

The cells cultured beforehand were collected by trypsin treatment, and the cell density was adjusted to 50,000 cells/ml. After the medium in the cells and petri dishes was discarded, the cell suspension was inoculated into the petri dishes at a cell number of 10,000 cells/cm$^2$, and then the medium was added.

(5) Culture

The cells were cultured at 37° C. for two days by using a $CO_2$ incubator.

(6) Evaluation

After each membrane was immersed in the medium for one day, deformation of each membrane was evaluated as a height of the membrane at the center portion protruding from the peripheral portion. A larger protrusion makes observation under an optical microscope more difficult, and if the protrusion exceeds 5 mm, the membrane is contacted to the culture dish, and thus substance supply from the back face becomes insufficient. Further, the cells were observed under an optical microscope to evaluate cell adhesion and toxicity. In this evaluation, the growth state on the culture dish was considered as a type.

(7) Results

The results are shown in Table 1. The carriers for cell culture of the present invention exhibited no toxicity, and favorable cell adhesion, as well as extremely little deformation of membrane. The results of observation of the cells cultured on the cell culture dish, and Samples 2 and 5 after UV sterilization under an optical microscope are shown in FIG. 1.

TABLE 1

| Level | Sample | Support | 1st, 3rd, 5th layer | 2th, 4th, 6th layer | 7th layer | 8th layer | 9th layer | Sterilization | Observation | Adhesion | Proliferation | State | |
|---|---|---|---|---|---|---|---|---|---|---|---|---|---|
| A | — | Culture dish | — | — | — | — | — | UV | ⊚ | ⊚ | 100 | Non-gel | Comparative |
| B | — | MEN-01 | — | — | — | — | — | " | X | ⊚ | 150 | Gel | " |
| C | 1 | Chitosan (NaOH was used) | None | None | None | None | None | " | ⊚ | X | 0 | " | " |
| D | 2 | Chitosan (buffer was used) | " | " | " | " | " | " | ⊚ | X | 0 | " | " |
| E | 3 | Chitosan (buffer was used) | Alginic acid | Chitosan | Alginic acid | " | " | " | ⊚ | ○ | 70 | " | Invention |
| F | 4 | Chitosan (buffer was used) | Alginic acid | " | Alginic acid | Chitosan | " | " | ⊚ | ⊚ | 100 | " | " |
| G | 5 | Chitosan (buffer was used) | Alginic acid | " | Alginic acid | Collagen | " | " | ⊚ | ⊚ | 180 | " | " |
| H | 6 | Chitosan (buffer was used) | Alginic acid | " | Alginic acid | Chitosan | Collagen | " | ⊚ | ⊚ | 150 | " | " |
| I | " | Chitosan (buffer was used) | Alginic acid | " | Alginic acid | " | " | Electron beam | ⊚ | ⊚ | 160 | " | " |
| J | 7 | Chitosan (NaOH was used) | Alginic acid | " | Alginic acid | Collagen | None | UV | ⊚ | ⊚ | 170 | " | " |
| K | 8 | Chitosan (NaOH was used) | Alginic acid | " | Alginic acid | Chitosan | Collagen | " | ⊚ | ⊚ | 150 | " | " |
| L | 9 | Chitosan/Alginic acid mixture | None | None | None | None | None | " | X | Δ | Unmeasurable | " | Comparative |

<Evaluation criteria for observation of cells>
⊚: Cells can be sufficiently observed over the entire membrane.
○: Cells can be observed over substantially entire membrane.
Δ: Cells in the center portion can be observed.
X: It is difficult to focus over the entire field of view.
<Evaluation criteria for cell adhesion>
⊚: 90% or more of cells adhere.
○: 70% or more of cells adhere.
Δ: 30% or more of cells adhere.
X: Adhering cells account for 10% or less.
<Evaluation criteria for cell proliferation>
The cell numbers are indicated as relative numbers based on the cell number of Level A after culture, which is taken as 100.

Example 3

Preparation of Carrier for Cell Culture and Evaluation of Physical Strength (1) Chitosan Gel Membrane (i) Preparation of Chitosan Application Solution 2.5 g of chitosan (Chirosan 100 produced by Wako Pure Chemical Industries) was dissolved in 98 g of 1 mass % acetic acid aqueous solution, and this solution was filtered through a filter PPE cartridge PPECG30S (capture efficiency for 25.7 μm according to ISO/TC131SC6 (1973) is 99.95%) to obtain an application solution.

(ii) Preparation of Chitosan Gel Membrane

The chitosan application solution was applied in a thickness of 1 mm on a polyethylene terephthalate substrate, and moisture of the coated layer was dried at 40° C. for 30 minutes. To this chitosan membrane, a plate made of stainless steel (SUS316) having a thickness of 100 μm was adhered as the inorganic layer, and the layer was dried at 40° C. for 5 hours. The dried chitosan membrane having an inorganic layer was delaminated from the polyethylene terephthalate substrate, immersed in a methanol solution containing 1.9 mass % sodium hydroxide for 30 minutes, and then immersed in a phosphate buffer of pH 1.0 isotonic to mammalian cells for 30 minutes. The chitosan gel membrane treated as described above was washed with running water for 30 minutes, and dried at room temperature to prepare Sample 1.

Further, a vinyl chloride substrate and a polyethylene terephthalate sheet having a thickness of 175 μm were used instead of the polyethylene terephthalate substrate and the stainless steel plate, respectively, to prepare Sample 2, and the polyethylene terephthalate substrate was used with a polyethylene terephthalate sheet having a thickness of 175 μm (aluminum was vapor-deposited on the surface in a thickness of 50 nm) instead of the stainless steel plate to obtain Sample 3. A membrane consisting solely of a chitosan membrane prepared in the same manner as Sample 1 except that the stainless steel plate was not used was used as Sample 4. Sample 4 was dried in a state that the four sides were pinched to prevent deformation of the membrane. The chitosan layers had a thickness of 20 μm in all the samples.

(2) Evaluation of Physical Strength of Carrier for Cell Culture (a) Adhesion

Each of Samples 1 to 4 was shaken at 50° C. for 24 hours in Eagle's minimum medium containing 10% fetal bovine serum, and then the delamination state of the chitosan membrane was observed.

(b) Strength

Each of Samples 1 to 4 was immersed in Eagle's minimum medium containing 10% bovine fetal blood serum, and the state of the membrane was observed when the membrane was lifted with a pair of tweezers.

The results are shown in Table 2. The carriers for cell culture of the present invention had superior effects that they had high strength, and in addition, they showed no disarrangement of the membrane.

Example 4

Preparation of Carrier for Cell Culture Using Cubstrate with Hole (1) Chitosan Gel Membrane Sample 5 was prepared in the same manner as Sample 1 in Example 1, except that a stainless steel plate having a hole with a diameter of 25 mm was used instead of the stainless steel substrate.

(2) Surface Modification of Chitosan Gel Membrane (i) Preparation of Alginic Acid Aqueous Solution Sodium arginate (sodium arginate produced by Wako Pure Chemical Industries, 100 to 150 cP) was dissolved in water at a concentration of 1 mass %.

(ii) Preparation of Chitosan Aqueous Solution 0.1 g of chitosan (Chirosan 100 produced by Wako Pure Chemical Industries) was dissolved in 99.9 g of 1 mass % acetic acid aqueous solution.

(iii) Preparation of Collagen Aqueous Solution

CellmatrixIC (type I collagen aqueous solution produced by Nitta Gelatin) was diluted with water to a concentration of 0.03 mg/ml.

(iv) Preparation of Alginic Acid-modified Gel Membrane

Samples 5 obtained in (1) mentioned above, without being dried, was immersed in the alginic acid aqueous solution for 5 minutes, and then washed with running water for 2 seconds. The sample was further immersed in the chitosan aqueous solution for 2 seconds, and then washed with running water for 2 seconds. The above operation was repeated three times. Subsequently, the sample was immersed in the alginic acid aqueous solution for 2 seconds, washed with running water for 1 hour, and then dried at room temperature to obtain Sample 6.

(v) Preparation of Chitosan-modified Gel Membrane

Samples 6, without being dried, was immersed in the chitosan aqueous solution for 2 seconds, washed with running water for 1 hour, and then dried at room temperature to obtain Sample 7.

(vi) Preparation of Collagen-modified Gel Membrane

Samples 6 and 7, without being dried, were immersed in the collagen aqueous solution for 1 hour, washed with running water for 1 hour, and then dried at 35° C., 30% RH to obtain Samples 8 and 9, respectively.

(3) Evaluation of Physical Strength of Carrier for Cell Culture

The results of evaluation for adhesion and strength performed in the same manner as that used in Example 3 are shown in Table 2. It can be seen that all of the carroers for cell culture of the present invention had favorable performance.

TABLE 2

| Sample | Adhesion | Strength | |
|---|---|---|---|
| 1 | Not delaminated | Good (No disarrangement in membrane) | Invention |
| 2 | Delaminated | Bad (Delaminated portions are curled) | Comparative |
| 3 | Not delaminated | Good (No disarrangement in membrane) | Invention |
| 4 | — | Bad (Membrane is partially broken, and unbroken portions are also curled) | Comparative |
| 5 | Not delaminated | Good (No disarrangement in membrane) | Invention |
| 6 | Not delaminated | Good (No disarrangement in membrane) | Invention |
| 7 | Not delaminated | Good (No disarrangement in membrane) | Invention |

Example 5

Sterilization

Samples 6 to 9 prepared in Example 4 were subjected to UV sterilization for 3 hours or electron beam sterilization at 20 kGy. As a result, no bacterium was found in each of the samples. In the samples not subjected to any sterilization treatment, 5,000 cells/m$^2$ of bacteria were observed.

Example 6

Culture of Cells Using Carrier for Cell Culture

Cells were cultured by using the carriers for cell culture as follows.

(1) Used Cell

CHL (Chinese Hamster Lung Cell)

(2) Used Medium

Eagle's minimum medium containing 10% fetal bovine serum (3) Carrier for Cell Culture Each of the carriers for cell culture of Samples 6 to 9 subjected to two kinds of sterilization in Example 5, and the permeable collagen membrane for cell culture, MEN-01, produced by KOKEN CO., LTD (comparative example) were put in a polystyrene cell culture dish. The carriers were added with the medium for immersion for 5 minutes, and then the medium was exchanged. This procedure was repeated three times, and then the carriers were left overnight to allow the medium to infiltrate into the carriers for cell culture. Combinations of the used carriers for cell culture and sterilization methods are shown in Table 3.

(4) Inoculation of Cells

The cells cultured beforehand were collected by trypsin treatment, and the cell density was adjusted to 50,000 cells/ml. After the medium in the cells and dishes was discarded, the cell suspension was inoculated in the dishes at a cell number of 10,000 cells/cm$^2$, and then the medium was added.

(5) Culture

The cells were cultured at 37° C. for two days by using a $CO_2$ incubator.

(6) Evaluation

After each membrane was immersed in the medium for one day, deformation of the membrane was evaluated as a height of the membrane at the center portion protruding from the peripheral portion. A larger protrusion makes observation under an optical microscope more difficult, and when the protrusion exceeds 5 mm, the membrane is contacted to the culture dish, and thus substance supply from the back face becomes insufficient. Further, the cells were observed under an optical microscope to evaluate cell adhesion and toxicity. In this evaluation, the growth state on the culture dish was considered as a type. The results are shown in Table 3. The carriers for cell culture of the present invention had no toxicity and favorable cell adhesion property, as well as gave extremely little deformation of membrane. Further, the provision of the hole in the inorganic layer gave higher substance permeability, and thus a long term culture was successful.

TABLE 3

| | | | Carrier for cell culture | | | | | | Cell | | | | |
|---|---|---|---|---|---|---|---|---|---|---|---|---|---|
| Level | Sample | Support | 1st, 3rd, 5th layer | 2th, 4th, 6th layer | 7th layer | 8th layer | 9th layer | Sterilization | Observation | Adhesion | Proliferation | Substance permeability | |
| A | — | Culture dish | — | — | — | — | — | UV | ◎ | ◎ | 100 | X | Comparative |
| B | — | MEN-01 | — | — | — | — | — | " | X | ◎ | 150 | ○ | " |
| C | 6 | Chitosan | Alginic acid | Chitosan | Alginic acid | — | — | " | ◎ | ○ | 80 | " | Invention |
| D | 7 | " | Alginic acid | " | Alginic acid | Chitosan | — | " | ◎ | ◎ | 100 | " | " |
| E | 8 | " | Alginic acid | " | Alginic acid | Collagen | — | " | ◎ | ◎ | 160 | " | " |
| F | 9 | " | Alginic acid | " | Alginic acid | Chitosan | Collagen | " | ◎ | ◎ | 150 | " | " |
| G | " | " | Alginic acid | " | Alginic acid | " | " | Electron beam | ◎ | ◎ | 170 | " | " |

<Evaluation criteria for observation of cells>
◎: Cells can be sufficiently observed over the entire membrane.
○: Cells can be observed over substantially entire membrane.
Δ: Cells in the center portion can be observed.
X: It is difficult to focus over the entire field of view.
<Evaluation criteria for cell adhesion>
◎: 90% or more of cells adhere.
○: 70% or more of cells adhere.
Δ: 30% or more of cells adhere.
X: Adhering cells account for 10% or less.
<Evaluation criteria for cell proliferation>
The cell numbers are indicated as relative numbers based on the cell number of Level A after culture, which is taken as 100.

Example 7

Carrier for Cell Culture Having Inorganic Layer With Multiple Holes

A carrier for cell culture was prepared in the same manner as that for Sample 9 mentioned in Example 6, except that a plate having holes with a diameter of 100 μm provided in 400 vertical rows and 400 transverse rows, 16,000 holes in total, at intervals of 300 μm was used instead of the stainless steel plate. When the resulting carrier for cell culture was similarly evaluated, favorable results in all of the physical strength, cell adhesion, and toxicity were obtained.

INDUSTRIAL APPLICABILITY

The carriers for cell culture of the present invention enables culture of cells using a different medium for each face of cells, and convenient observation of growth state of the cells under an optical microscope. Further, the carrier for cell culture according to the second aspect of the present invention is characterized by high adhesion and strength, as well as little deformation of membrane. These carriers for cell culture are also characterized to have reduced cytotoxicity and enable a long term cell culture.

What is claimed is:

1. A carrier for cell culture comprising a water-containing polymer gel containing chitosan, wherein the carrier for cell culture is generally in a form of a plane and the water-containing polymer gel is coated with collagen and/or alginic acid.

2. The carrier for cell culture according to claim 1, which comprises two or more coated layers.

3. The carrier for cell culture according to claim 2, wherein an outermost layer is a collagen-coating layer or an alginic acid-coating layer.

4. The carrier for cell culture according to claim 2, wherein an outermost layer is an alginic acid-coating layer.

5. The carrier for cell culture according to claim 2, which comprises a chitosan-coating layer as an outermost layer formed on an alginic acid-coating layer.

6. A method for culturing cells comprising using the carrier according to claim 1 for cell culture.

* * * * *